(12) United States Patent
Watanabe et al.

(10) Patent No.: US 10,514,349 B2
(45) Date of Patent: Dec. 24, 2019

(54) GAS SENSOR

(71) Applicant: NGK INSULATORS, LTD., Nagoya-shi, Aichi (JP)

(72) Inventors: Yusuke Watanabe, Nagoya (JP); Takao Murase, Konan (JP); Masashi Yasui, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 295 days.

(21) Appl. No.: 15/248,160

(22) Filed: Aug. 26, 2016

(65) Prior Publication Data

US 2017/0089852 A1 Mar. 30, 2017

(30) Foreign Application Priority Data

Sep. 29, 2015 (JP) .................................. 2015-191249

(51) Int. Cl.
| | |
|---|---|
| *G01N 27/00* | (2006.01) |
| *G01N 27/02* | (2006.01) |
| *G01N 33/00* | (2006.01) |
| *G01N 27/407* | (2006.01) |

(52) U.S. Cl.
CPC ....... *G01N 27/028* (2013.01); *G01N 27/4077* (2013.01); *G01N 33/0037* (2013.01)

(58) Field of Classification Search
CPC ............. G01N 27/028; G01N 27/4077; G01N 33/0037
See application file for complete search history.

(56) References Cited

U.S. PATENT DOCUMENTS

| | | |
|---|---|---|
| 2002/0017128 A1 | 2/2002 | Shirai |
| 2002/0036138 A1 | 3/2002 | Kuroki et al. |
| 2007/0246361 A1 | 10/2007 | Hirose et al. |

(Continued)

FOREIGN PATENT DOCUMENTS

| | | | |
|---|---|---|---|
| JP | 2001-356109 A | | 12/2001 |
| JP | 2001356109 A | * | 12/2001 |
| JP | 2002-82089 A | | 3/2002 |

(Continued)

OTHER PUBLICATIONS

Notification dated Jun. 25, 2019 for the corresponding Japanese Patent Application No. 2015-191249, including a submission of Publication by Third Party.

(Continued)

*Primary Examiner* — Blake A Tankersley
(74) *Attorney, Agent, or Firm* — Global IP Counselors, LLP

(57) ABSTRACT

A gas sensor 10 includes a tubular protective cover 30 having an element chamber 37 therein and configured to allow a measured gas to flow from the outside into the element chamber 37; and a long sensor element 20 including a detecting portion 23 located in the element chamber 37 and configured to detect a specified gas concentration in the measured gas. An inclination angle θt of an axial direction of the sensor element 20 (i.e., a direction parallel to an element axis A1) in the element chamber 37 with respect to an axial direction of the protective cover 30 (i.e., a direction parallel to a cover axis A2) is 1° or greater.

5 Claims, 3 Drawing Sheets

(56) References Cited

U.S. PATENT DOCUMENTS

2012/0297861 A1† 11/2012 Murai
2013/0019655 A1    1/2013 Nakagawa et al.

FOREIGN PATENT DOCUMENTS

| JP | 2003-107034 A | 4/2003 |
| JP | 2004-4072 A | 1/2004 |
| JP | 3932881 B2 | 3/2007 |
| JP | 2007-101353 A | 4/2007 |
| JP | 2007-292463 A | 11/2007 |
| JP | 2008-170341 A | 7/2008 |
| JP | 4473471 B2 | 3/2010 |
| JP | 4473471 B2 † | 6/2010 |
| JP | 2010-243422 A | 10/2010 |
| JP | 2013-40922 A | 2/2013 |

OTHER PUBLICATIONS

Notice of Reasons for Refusal for the corresponding Japanese application No. 2015-191249, dated Oct. 1, 2019.

\* cited by examiner
† cited by third party

GAS SENSOR

BACKGROUND OF THE INVENTION

1. Field of the Invention

The present invention relates to a gas sensor.

2. Description of the Related Art

Gas sensors have been known, which detect the concentration of a specified gas, such as NOx, in a gas to be measured (hereinafter referred to as a measured gas), such as an automobile exhaust gas. For example, Patent Literature (PTL) 1 describes a gas sensor that includes a sensor element secured to a tubular housing, and a tubular measured-gas-side cover (protective cover) configured to cover a distal end of the sensor element.

CITATION LIST

Patent Literature

[PTL 1] Japanese Patent No. 3932881

SUMMARY OF THE INVENTION

In this gas sensor, when a measured gas circulates inside the protective cover and reaches a detecting portion of the sensor element, the detecting portion detects a specified gas concentration. Due to the length of time required for the measured gas to reach the detecting portion, responsiveness in detecting the specified gas concentration may be low.

The present invention has been made to solve the problem described above. A primary object of the present invention is to improve responsiveness in detecting a specified gas concentration.

The present inventors carried out studies and predicted that because the flow of the measured gas in an inner space of the protective cover having the sensor element therein was laminar, the measured gas could not easily reach the detecting portion inside, or on the surface of, the distal end of the sensor element and thus the responsiveness described above was lowered. As a result of further studies, the present inventors found that positioning the sensor element of the gas sensor of the related art on the axial line of the protective cover tended to cause the flow of the measured gas to be laminar. The present inventors then discovered that, by inclining the sensor element from the axial direction of the protective cover, responsiveness in detecting a specified gas concentration could be improved. This led to the completion of the present invention.

That is, the present invention adopts the following measures to achieve the primary object described above.

A gas sensor of the present invention comprises:

a tubular protective cover having an element chamber therein and configured to allow a measured gas to flow from the outside into the element chamber; and a long sensor element including a detecting portion located in the element chamber and configured to detect a specified gas concentration in the measured gas, wherein an inclination angle θt of an axial direction of the sensor element in the element chamber with respect to an axial direction of the protective cover is 1° or greater.

In this gas sensor, the axial direction of the sensor element in the element chamber is inclined with respect to the axial direction of the protective cover, and the inclination angle θt is 1° or greater. Thus, the sensor element can disturb the flow of the measured gas in the element chamber, and this makes the flow of the measured gas less likely to be laminar (i.e., more likely to be turbulent). Therefore, the measured gas can more easily reach the detecting portion, and the responsiveness of the gas sensor in detecting a specified gas concentration can be improved.

In the gas sensor according to the present invention, the inclination angle θt may be 3° or greater. In this case, the occurrence of laminar flow of the measured gas can be more effectively reduced by the inclination of the sensor element, and the responsiveness of the gas sensor can be further improved.

In the gas sensor according to the present invention, the inclination angle θt may be 15° or less. In this case, an increase in pressure loss in the element chamber caused by the inclination of the sensor element can be reduced. It is thus possible to reduce slowing down of the flow of the measured gas caused by the pressure loss, and reduce degradation in the responsiveness of the gas sensor.

The gas sensor according to the present invention may further include a protective layer having a greater thickness at a portion covering a surface of the sensor element on an inclination side in the element chamber than at a portion covering a surface of the sensor element opposite the inclination side in the element chamber. Since this unevenness in the thickness of the protective layer disturbs the flow of the measured gas in the element chamber and makes it less likely to be laminar, the responsiveness of the gas sensor can be further improved.

In the gas sensor according to the present invention, the protective cover may have an element chamber inlet open to the element chamber and serving as a passage of the measured gas; and an element chamber outlet open to the element chamber, serving as a passage of the measured gas, and located closer to a distal end of the protective cover than the element chamber inlet is. Generally, when the element chamber inlet and the element chamber outlet have this positional relationship, the flow of the measured gas tends to be a laminar flow along the axial direction of the protective cover, and this tends to lower the responsiveness of the gas sensor. Therefore, it is of great significance to apply the present invention.

In the gas sensor according to the present invention, the sensor element may have a plate-like shape and a portion of the sensor element, the portion being located in the element chamber, may be inclined in a thickness direction of the sensor element with respect to the axial direction of the protective cover. In this case, for example, as compared to the case where the sensor element is inclined in a direction perpendicular to the thickness direction, the area of a surface of the sensor element intersecting the axial direction of the protective cover is large. This disturbs the flow of the measured gas in the element chamber, makes it less likely to be laminar, and further improves the responsiveness of the gas sensor.

DETAILED DESCRIPTION OF THE INVENTION

Figure 1:
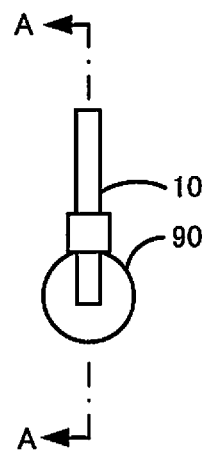
FIG. 1 is a schematic diagram illustrating how a gas sensor 10 is attached to a pipe 90.
Figure 2:
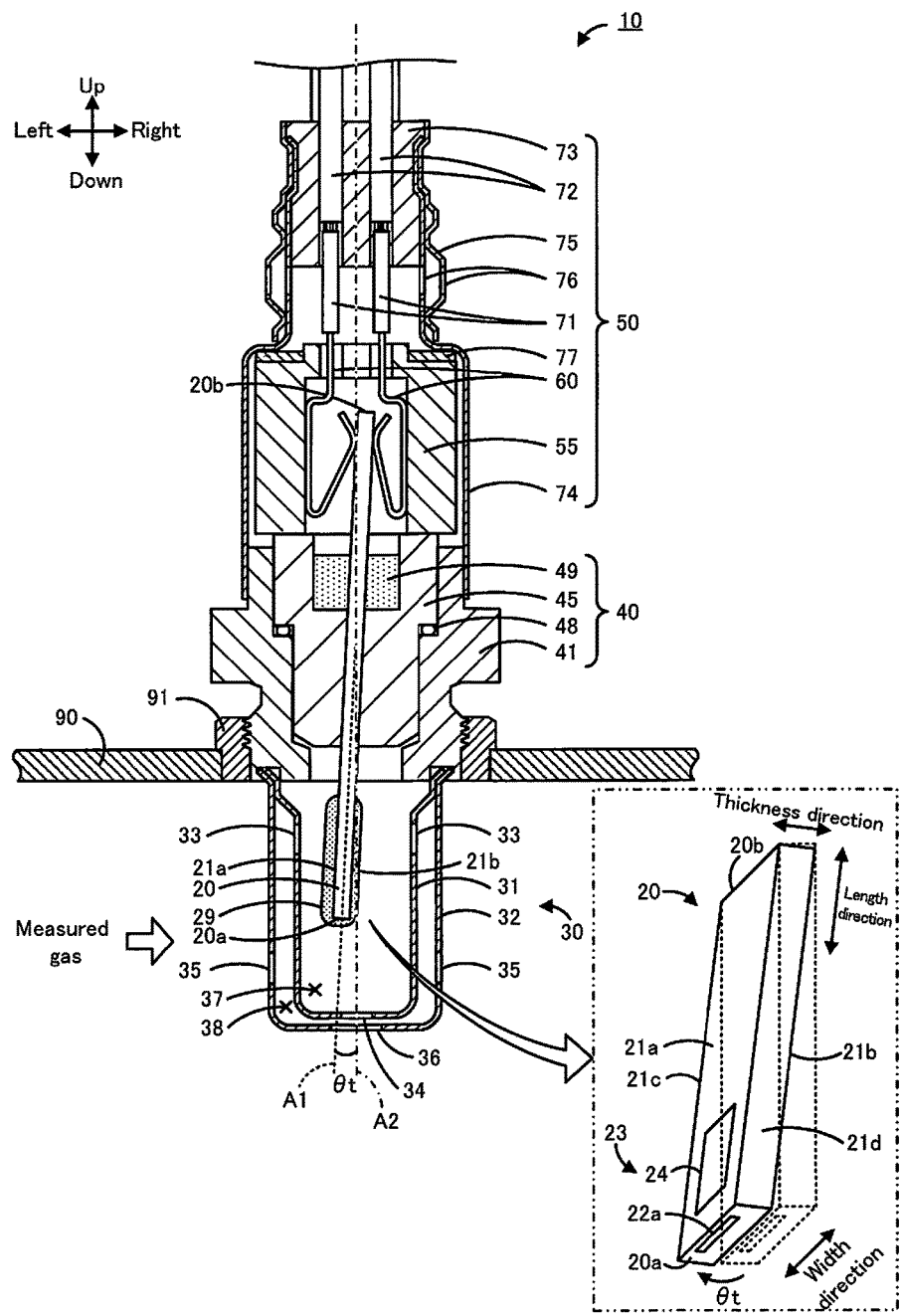
FIG. 2 is a longitudinal cross-sectional view of the gas sensor 10.
Figure 3:
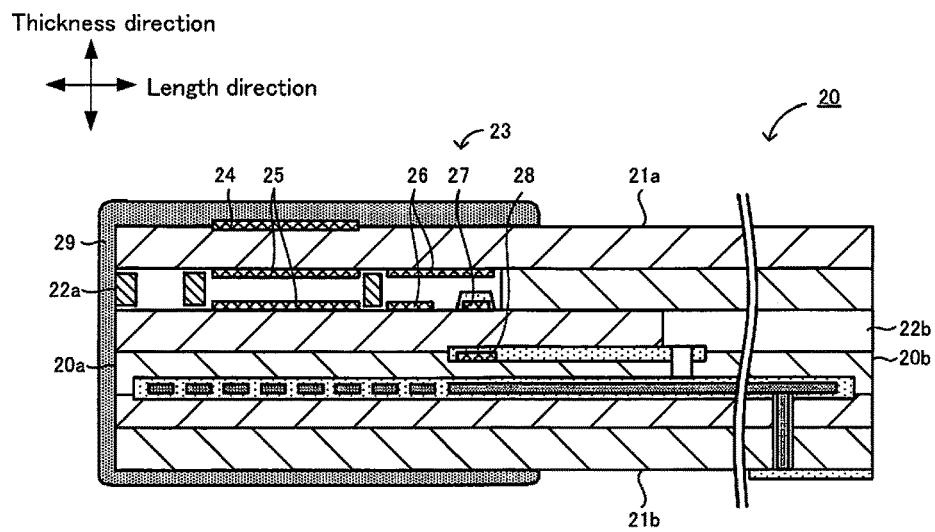
FIG. 3 is a cross-sectional view perpendicular to a width direction of a sensor element 20.

Embodiments of the present invention will now be described with reference to the drawings. FIG. 1 is a schematic diagram illustrating how a gas sensor 10 according to an embodiment of the present invention is attached to a pipe 90. FIG. 2 is a longitudinal cross-sectional view of the gas sensor 10 taken along line A-A of FIG. 1. A frame indicated by a two-dot chain line in the lower right part of FIG. 2 provides a schematic perspective view of a sensor element 20. FIG. 3 is a cross-sectional view perpendicular to a width direction of the sensor element 20. In the present embodiment, the up-down direction and the right-left direction are as shown in FIG. 2.

As illustrated in FIG. 1, the gas sensor 10 is attached to the pipe 90, such as a vehicle exhaust gas pipe, and used to measure a specified gas concentration, which is the concentration of a specified gas, such as NOx or $O_2$, contained in an exhaust gas serving as a measured gas. In the present embodiment, the gas sensor 10 is used to measure a NOx concentration as a specified gas concentration.

As illustrated in FIG. 2, the gas sensor 10 includes the sensor element 20; a protective layer 29 configured to cover at least part of the surface of the sensor element 20; a protective cover 30 configured to protect a distal portion (lower end portion in FIG. 2), including a distal face 20a, of the sensor element 20; an element sealing unit 40 configured to seal and secure the sensor element 20; and an assembled unit 50 configured to protect a proximal portion (upper end portion in FIG. 2), including a proximal face 20b, of the sensor element 20 and extract an electric signal from the sensor element 20.

The sensor element 20 has a laminated structure with a plurality of oxygen ion-conducting solid electrolyte layers, such as zirconia ($ZrO_2$) layers. The sensor element 20 is a long plate-like element (in the shape of a rectangular parallelepiped) having the distal face 20a at the lower end thereof, the proximal face 20b at the upper end thereof, and first to fourth faces 21a to 21d perpendicular to the distal face 20a and the proximal face 20b. In the sensor element 20, a direction along the longest of the three sides of the rectangular parallelepiped (e.g., a side shared by the first face 21a and the fourth face 21d) is defined as a length direction, a direction along the shortest of the three sides of the rectangular parallelepiped (e.g., a side shared by the distal face 20a and the fourth face 21d) is defined as a thickness direction, and a direction along the remaining one of the three sides of the rectangular parallelepiped (e.g., a side shared by the distal face 20a and the first face 21a) is defined as a width direction. The axial direction of the sensor element 20 is inclined by an inclination angle θt with respect to the axial direction of the protective cover 30. The inclination angle θt will be described in detail later on. The sensor element 20 may be, for example, 25 mm to 100 mm long, 2 mm to 10 mm wide, and 0.5 mm to 5 mm thick. As illustrated in FIGS. 2 and 3, the sensor element 20 has a measured gas introduction port 22a for introducing therein the measured gas, a reference gas introduction port 22b for introducing therein a reference gas (atmosphere) serving as a reference for detection of a specified gas concentration, and a detecting portion 23 configured to detect a specified gas concentration in the measured gas. The measured gas introduction port 22a is open in the distal face 20a of the sensor element 20, and is located in an element chamber 37 which is a space inside an inner protective cover 31. The reference gas introduction port 22b is open in the proximal face 20b of the sensor element 20 as illustrated in FIG. 3, and is located in a space inside an atmosphere-side cover 74.

The detecting portion 23 includes at least one electrode, and is disposed in the element chamber 37 to detect a specified gas concentration in the measured gas in the element chamber 37. In the present embodiment, the detecting portion 23 includes an outer electrode 24 disposed on the first face 21a; and inner main pump electrodes 25, inner auxiliary pump electrodes 26, a measurement electrode 27, and a reference electrode 28 disposed inside the sensor element 20. The measured gas in the element chamber 37 reaches the outer electrode 24 and the measured gas introduction port 22a. The measured gas introduced through the measured gas introduction port 22a into the inside of the sensor element 20 reaches the inner main pump electrodes 25, the inner auxiliary pump electrodes 26, and the measurement electrode 27 in this order. The reference gas introduced through the reference gas introduction port 22b reaches the reference electrode 28. The principle on the basis of which the detecting portion 23 detects a specified gas concentration will not be described in detail, as it is well known. For example, the detecting portion 23 detects a specified gas concentration in the following manner. On the basis of a voltage applied between the outer electrode 24 and the inner main pump electrodes 25, the detecting portion 23 pumps oxygen in the measured gas around the inner main pump electrodes 25 into or out of the detecting portion 23 (to the element chamber 37). Also, on the basis of a voltage applied between the outer electrode 24 and the inner auxiliary pump electrodes 26, the detecting portion 23 pumps oxygen in the measured gas around the inner auxiliary pump electrodes 26 into or out of the detecting portion 23 (to the element chamber 37). Thus, the measured gas having an oxygen concentration adjusted to a predetermined value reaches the vicinity of the measurement electrode 27. The measurement electrode 27 serves as a NOx reduction catalyst to reduce a specified gas (NOx) in the measured gas reached. Then, an electromotive force generated between the measurement electrode 27 and the reference electrode 28 in accordance with the oxygen concentration after the reduction or a current based on the electromotive force is generated as an electric signal by the detecting portion 23. The electric signal thus generated by the detecting portion 23 is a signal representing a value corresponding to a specified gas concentration in the measured gas (i.e., a value from which the specified gas concentration can be derived), and is equivalent to a value detected by the detecting portion 23. The electric signal is output to the outside through a conductive electrode (not shown) disposed on the surface of the proximal portion of the sensor element 20.

The protective layer 29 is a porous layer that covers at least part of the surface of the sensor element 20. The protective layer 29 covers the entire distal face 20a of the sensor element 20 and most parts of the first to fourth faces 21a to 21d positioned in the element chamber 37. The protective layer 29 also covers the outer electrode 24 and the measured gas introduction port 22a, but since the protective layer 29 is a porous layer, the measured gas can pass through the protective layer 29 to reach the outer electrode 24 and the measured gas introduction port 22a. The protective layer 29 serves to protect the sensor element 20 from, for example, moisture or oil components in the measured gas. The protective layer 29 is a porous layer of ceramic, such as alumina. The protective layer 29 has a greater thickness at a portion covering the first face 21a (i.e., a portion on the left side of the sensor element 20 in FIG. 2) than at a portion covering the second to fourth faces 21b to 21d and the distal face 20a. Therefore, the protective layer 29 has a greater thickness at a portion covering a surface (first face 21a) of the sensor element 20 on the inclination side in the element chamber 37 than at a portion covering a surface (second face 21b) of the sensor element 20 opposite the inclination side in the element chamber 37.

The protective cover 30 is a cylindrical member made of metal, such as stainless steel, and configured to allow the measured gas to flow from outside into the element chamber 37. The protective cover 30 includes the inner protective cover 31 which is a cylindrical member with a bottom and configured to cover the distal portion of the sensor element 20, and an outer protective cover 32 which is a cylindrical member with a bottom and configured to cover the inner protective cover 31. The inner protective cover 31 has the element chamber 37 therein. The element chamber 37 is a space surrounded by the inner periphery of the inner protective cover 31. The distal portion of the sensor element 20, including the distal face 20a and the detecting portion 23, is disposed in the element chamber 37. The inner protective cover 31 and the outer protective cover 32 are provided with a gas chamber 38 therebetween, which is a space surrounded by the inner protective cover 31 and the outer protective cover 32.

The inner protective cover 31 has a plurality of element chamber inlets 33 in the periphery thereof, and an element chamber outlet 34 at the bottom thereof. The element chamber inlets 33 and the element chamber outlet 34 are open to the element chamber 37 and the gas chamber 38. The element chamber inlets 33 serve as passages of the measured gas from the gas chamber 38 to the element chamber 37. The element chamber outlet 34 serves as a passage of the measured gas from the element chamber 37 to the gas chamber 38. The element chamber inlets 33 are located closer to the proximal face 20b than the distal face 20a (and the measured gas introduction port 22a) of the sensor element 20 is (i.e., located above the distal face 20a). At the same time, the element chamber inlets 33 are located above the outer electrode 24, which is an electrode of the detecting portion 23 and is disposed on the surface of the sensor element 20. The element chamber outlet 34 is located below the element chamber inlets 33, that is, closer to the distal end of the protective cover 30 than the element chamber inlets 33 are. At the same time, the element chamber outlet 34 is located below the distal face 20a of the sensor element 20. The element chamber inlets 33 and the element chamber outlet 34 are circular holes. The inside diameter of the inner protective cover 31 may be, for example, from 5 mm to 10 mm. The vertical distance between the element chamber inlets 33 and the element chamber outlet 34 (i.e., the distance in the axial direction of the inner protective cover 31) may be, for example, from 10 mm to 20 mm.

The outer protective cover 32 has a plurality of outer inlets 35 in the periphery thereof, and an outer outlet 36 at the bottom thereof. The outer inlets 35 and the outer outlet 36 are open to the gas chamber 38 and the outside of the outer protective cover 32 (i.e., inside of the pipe 90). The outer inlets 35 serve as passages of the measured gas from the outside to the gas chamber 38. The outer outlet 36 serves as a passage of the measured gas from the gas chamber 38 to the outside. The outer inlets 35 are located below the element chamber inlets 33. The outer outlet 36 is located below the element chamber outlet 34 and the outer inlets 35. The outer inlets 35 and the outer outlet 36 are circular holes. The inside diameter of the outer protective cover 32 may be, for example, from 7 mm to 15 mm.

The element sealing unit 40 includes a housing 41, a first insulator 45, a sealing member 48, and a seal material 49. The sensor element 20 is positioned around the central axis of the element sealing unit 40, and vertically passes through the element sealing unit 40. The housing 41 is a cylindrical metal member with a lower end to which the upper end of the protective cover 30 is attached. The housing 41 is welded to the pipe 90 and inserted into a securing member 91 having female threads on the inner periphery thereof. Thus, the gas sensor 10 is secured to the pipe 90, with the distal portion of the sensor element 20 and the protective cover 30 of the gas sensor 10 protruding into the pipe 90. The first insulator 45 is a columnar member disposed inside the housing 41. The sensor element 20 passes through the inside of the first insulator 45. The first insulator 45 is made of an insulating ceramic, such as alumina, steatite, or zirconia. The sealing member 48 is a ring-shaped member made of metal, such as stainless steel, nickel, or copper. The sealing member 48 is pushed upward and downward by the housing 41 and the first insulator 45, respectively, and configured to hermetically seal the gap between the housing 41 and the first insulator 45. The seal material 49 is obtained by molding ceramic powder, such as talc, alumina, or boron nitride powder. The seal material 49 is charged into the space between the inner periphery of the first insulator 45 and the sensor element 20, whereby the space between the first insulator 45 and the sensor element 20 is hermetically sealed. The first insulator 45 and the seal material 49 each have an inclined through-hole, into which the sensor element 20 is inserted and secured in place at the inclination angle θt.

The assembled unit 50 includes a second insulator 55, a plurality of contact fittings 60, a plurality of connection terminals 71, a plurality of lead wires 72, a rubber stopper 73, an atmosphere-side cover 74, an outer cover 75, and a disc spring 77. The second insulator 55 is a cylindrical member with a bottom, and is made of an insulating ceramic as in the case of the first insulator 45. The second insulator 55 is in contact, on the lower face thereof, with the upper face of the first insulator 45, and is positioned to be coaxial with the first insulator 45. The contact fittings 60 are metal plates each bent at multiple points and having a plate spring portion folded inward. A plurality of (e.g., two or three) contact fittings 60 are disposed on each of the right and left sides of the sensor element 20, and connected to corresponding conductive electrodes (not shown) disposed on the first and second faces 21a and 21b of the sensor element 20. The plate spring portions of the contact fittings 60 are supported by the second insulator 55 by a reactive force against their elastic force, and are electrically connected to the conductive electrodes on the sensor element 20 by pushing the sensor element 20 from both the right and left sides. An end portion of each of the contact fittings 60 passes through a hole on the upper side of the second insulator 55 to protrude therefrom and is electrically connected to the corresponding lead wire 72, with the corresponding connection terminal 71 interposed therebetween. The lead wires 72 vertically pass through the rubber stopper 73 that closes the upper end of the atmosphere-side cover 74 and the outer cover 75, and extend to the outside (i.e., to the outside of the pipe 90, or to the atmosphere). The atmosphere-side cover 74 covers a part of the outer periphery of the element sealing unit 40 on the proximal side (upper side) of the sensor element 20. At the same time, the atmosphere-side cover 74 covers the second insulator 55 and the rubber stopper 73. The outer cover 75 covers the outer periphery of the upper side of the atmosphere-side cover 74. The atmosphere-side cover 74 and the outer cover 75 each have a plurality of atmosphere introduction holes 76, through which the reference gas (atmosphere) passes and is introduced through the reference gas introduction port 22b into the sensor element 20. The atmosphere-side cover 74 and the outer cover 75 have a swaged portion with a reduced diameter near the upper end thereof. With this swaged portion, the rubber stopper 73 is secured in place. The disc spring 77 is sandwiched between the atmosphere-side cover 74 above and the second insulator 55 below. By pushing the second insulator 55 downward, the disc spring 77 secures the second insulator 55 and the first insulator 45 in place.

The inclination angle θt of the sensor element 20 will now be described in detail. The inclination angle θt is the angle of inclination of the axial direction of the sensor element 20 in the element chamber 37 with respect to the axial direction of the protective cover 30. FIG. 2 shows an element axis A1 which is the central axis of the sensor element 20. The element axis A1 is an axis parallel to the length direction of the sensor element 20, and a direction parallel to the element axis A1 is the axial direction of the sensor element 20. In the present embodiment, the sensor element 20 has no warpage, and a portion of the sensor element 20 located in the element chamber 37 has the same axial direction as the other portion (e.g., the proximal portion including the proximal face 20b) not located in the element chamber 37. Therefore, like the axial direction of the entire sensor element 20, the axial direction of the sensor element 20 in the element chamber 37 (i.e., the axial direction of the portion of the sensor element 20 located in the element chamber 37) is parallel to the element axis A1. Also in the present embodiment, the central axis of the gas sensor 10 coincides with the central axis of the protective cover 30 (i.e., the inner protective cover 31 and the outer protective cover 32), and is indicated as a cover axis A2 in FIG. 2. The cover axis A2 is parallel to the up-down direction in FIG. 2, and this up-down direction is the axial direction of the protective cover 30. The axial direction of the sensor element 20 (i.e., a direction parallel to the element axis A1) is inclined by the inclination angle θt with respect to the axial direction of the protective cover 30 (i.e., a direction parallel to the cover axis A2). The inclination angle θt is 1° or greater. The inclination angle θt may be 20° or less. The sensor element 20 is inclined in the thickness direction of the sensor element 20. That is, as shown in the frame indicated by a two-dot chain line in FIG. 2, the sensor element 20 pivots from a position in which the element axis A1 is parallel to the cover axis A2 (i.e., the position of the sensor element 20 indicated by a broken line) in the thickness direction (parallel to the distal face 20a, the third face 21c, and the fourth face 21d). In the present embodiment, the sensor element 20 is inclined in the thickness direction, particularly in the direction in which the distal portion of the sensor element 20 is moved from the position of the second face 21b toward the first face 21a. Alternatively, the sensor element 20 may be inclined in the thickness direction, particularly in the direction in which the distal portion of the sensor element 20 is moved from the position of the first face 21a toward the second face 21b. Note that the element axis A1 and the cover axis A2 do not need to intersect each other. Even when the element axis A1 and the cover axis A2 do not intersect each other, the inclination angle θt can be determined as long as the axial direction of the protective cover 30 (i.e., a direction parallel to the cover axis A2) and the axial direction of the sensor element 20 in the element chamber 37 (i.e., a direction parallel to the element axis A1) are inclined with respect to each other.

An example of using the gas sensor 10 configured as described above will now be described. When the measured gas flows in the pipe 90, with the gas sensor 10 attached to the pipe 90 as illustrated in FIGS. 1 and 2, the measured gas circulates inside the protective cover 30. Specifically, the measured gas in the pipe 90 flows through the outer inlets 35 into the gas chamber 38, from which it flows through the element chamber inlets 33 into the element chamber 37. In the element chamber 37, the measured gas flows from the element chamber inlets 33 toward the element chamber outlet 34, from which it flows through the outer outlet 36 to the outside (i.e., to the inside of the pipe 90). In the present embodiment, the protective cover 30 is of a so-called aspirator type (which may also be referred to as a differential-pressure aspiration type). That is, by using a phenomenon in which a static pressure in the vicinity of the central axis of the pipe 90 is lower than that in the vicinity of the inner periphery of the pipe 90, the protective cover 30 is configured such that the measured gas flows in through the outer inlets 35 in the vicinity of the inner periphery of the pipe 90 and flows out through the outer outlet 36 in the vicinity of the central axis of the pipe 90. Then, when the measured gas reaches the detecting portion 23 during its circulation in the element chamber 37, or more specifically, when the measured gas reaches the outer electrode 24 and also reaches the inside of the sensor element 20 through the measured gas introduction port 22a, the detecting portion 23 generates an electric signal corresponding to a specified gas concentration in the measured gas as described above. By extracting the electric signal through the contact fittings 60, the connection terminals 71, and the lead wires 72, the specified gas concentration is detected on the basis of the electric signal.

If the central axis of the sensor element coincides with the central axis of the protective cover as in the gas sensor of the related art (i.e., if the inclination angle θt is 0°), the flow of the measured gas in the element chamber tends to be laminar. The more laminar the flow of the measured gas, the more time it takes for the measured gas flowing around the sensor element to reach the detecting portion at the distal end of the sensor element. When the measured gas cannot easily reach the detecting portion, responsiveness in detecting the specified gas concentration tends to be lowered. That is, for example, even if the specified gas concentration in the measured gas changes, the corresponding electric signal generated by the sensor element cannot be changed immediately. However, in the gas sensor 10 of the present embodiment in which the inclination angle θt is 1° or greater, the sensor element 20 in the element chamber 37 can disturb the flow of the measured gas (i.e., downward flow from the element chamber inlets 33 toward the element chamber outlet 34 in the present embodiment). This makes the flow of the measured gas in the element chamber 37 less likely to be laminar (i.e., more likely to be turbulent). Therefore, the measured gas flowing around the sensor element 20 can more easily reach the detecting portion 23 at the distal end of the sensor element 20, and the responsiveness of the gas sensor 10 in detecting the specified gas concentration can be improved.

The inclination angle θt is preferably 3° or greater. In this case, the occurrence of laminar flow of the measured gas can be more effectively reduced by the inclination of the sensor element 20, and the responsiveness of the gas sensor 10 can be further improved. The inclination angle θt is more preferably 5° or greater, and still more preferably 9° or greater. At the same time, the inclination angle θt is preferably 15° or less. In this case, an increase in pressure loss in the element chamber 37 caused by the inclination of the sensor element 20 can be reduced. It is thus possible to reduce slowing down of the flow of the measured gas caused by the pressure loss, and reduce degradation in the responsiveness of the gas sensor 10. The inclination angle θt is more preferably 13° or less, and still more preferably 11° or less. As in the present embodiment, it is preferable that the direction of inclination of the sensor element 20 in the element chamber 37 be opposite the direction of flow of the measured gas (i.e., from left to right in FIG. 2). Also, as in the present embodiment, it is preferable that the direction of inclination of the sensor element 20 in the element chamber 37 be a direction toward one of the element chamber inlets 33.

In the gas sensor 10 of the present embodiment described above in detail, where the inclination angle θt is 1° or greater, the measured gas can easily reach the detecting portion 23 of the sensor element 20 and the responsiveness of the gas sensor 10 in detecting the specified gas concentration is improved. If the inclination angle θt is 3° or greater, the responsiveness of the gas sensor 10 is further improved. At the same time, if the inclination angle θt is 15° or less, degradation in the responsiveness of the gas sensor 10 caused by an increase in pressure loss can be reduced. Generally, if the measured gas has at least one of a low flow velocity, a low flow rate, and a low pressure, it is particularly difficult for the measured gas to reach the detecting portion 23. Therefore, in such a case, it is of particularly great significance to reduce the occurrence of laminar flow in the element chamber 37 by setting the inclination angle θt to 1° or greater.

The gas sensor 10 includes the protective layer 29 having a greater thickness at a portion covering the surface (first face 21a) of the sensor element 20 on the inclination side in the element chamber 37 than at a portion covering the surface (second face 21b) of the sensor element 20 opposite the inclination side in the element chamber 37. Since this unevenness in the thickness of the protective layer 29 disturbs the flow of the measured gas in the element chamber 37 and makes it less likely to be laminar, the responsiveness of the gas sensor 10 can be further improved.

Also in the gas sensor 10, the protective cover 30 has the element chamber inlets 33 open to the element chamber 37 and serving as passages of the measured gas; and the element chamber outlet 34 open to the element chamber 37, serving as a passage of the measured gas, and located closer to the distal end of the protective cover 30 than the element chamber inlets 33 are. Generally, when the element chamber inlets and the element chamber outlet have this positional relationship, the flow of the measured gas tends to be a laminar flow along the axial direction of the protective cover, and this may lower the responsiveness of the gas sensor. Therefore, it is of great significance, in the protective cover 30 configured as described above, to reduce the occurrence of laminar flow in the element chamber 37 by setting the inclination angle θt to 1° or greater.

Also in the gas sensor 10, the sensor element 20 has a plate-like shape, and a portion of the sensor element 20 located in the element chamber 37 is inclined in the thickness direction of the sensor element 20 with respect to the axial direction of the protective cover 30. Therefore, for example, as compared to the case where the sensor element 20 is inclined in a direction (width direction) perpendicular to the thickness direction, the area of a surface of the sensor element 20 intersecting the axial direction of the protective cover 30 is large. Specifically, for example, if the sensor element 20 is inclined in the width direction, the third face 21c or the fourth face 21d intersects the axial direction of the protective cover 30, whereas if the sensor element 20 is inclined in the thickness direction, the first face 21a (as in the present embodiment) or the second face 21b having a greater area than the third and fourth faces 21c and 21d intersects the axial direction of the protective cover 30. In the latter case, since the flow of the measured gas in the element chamber 37 is disturbed and is less likely to be laminar, the responsiveness of the gas sensor 10 is further improved.

The present invention is by no means limited to the embodiments described above, and can be carried out in various ways within the technical scope of the present invention.

For example, although the sensor element 20 is inclined in the thickness direction in the embodiments described above, the present invention is not limited to this. That is, the sensor element 20 may be inclined in a direction (width direction) perpendicular to the thickness direction, or may be inclined in both the thickness and width directions.

Although the central axis of the gas sensor 10 coincides with the central axis of the protective cover 30 (i.e., the inner protective cover 31 and the outer protective cover 32) in the embodiments described above, the present invention is not limited to this. The inclination angle θt is determined on the basis of the direction of the central axis (element axis A1) of the sensor element 20 and the direction of the central axis (cover axis A2) of the protective cover 30. For example, the central axis of the gas sensor 10 does not necessarily need to coincide with, or does not necessarily need to be parallel to, the central axis of the protective cover 30. Also, the central axis of the gas sensor 10 may be parallel to (or may coincide with) the central axis of the sensor element 20, as long as the axial direction of the sensor element 20 and the axial direction of the protective cover 30 are inclined with respect to each other. Although the central axis of the inner protective cover 31 coincides with that of the outer protective cover 32 in the embodiments described above, the present invention is not limited to this. If the axial direction of the inner protective cover 31 differs from that of the outer protective cover 32, the axial direction of the inner protective cover 31 (or in other words, the axial direction of the element chamber 37) is defined as "the axial direction of the protective cover".

Figure 4:
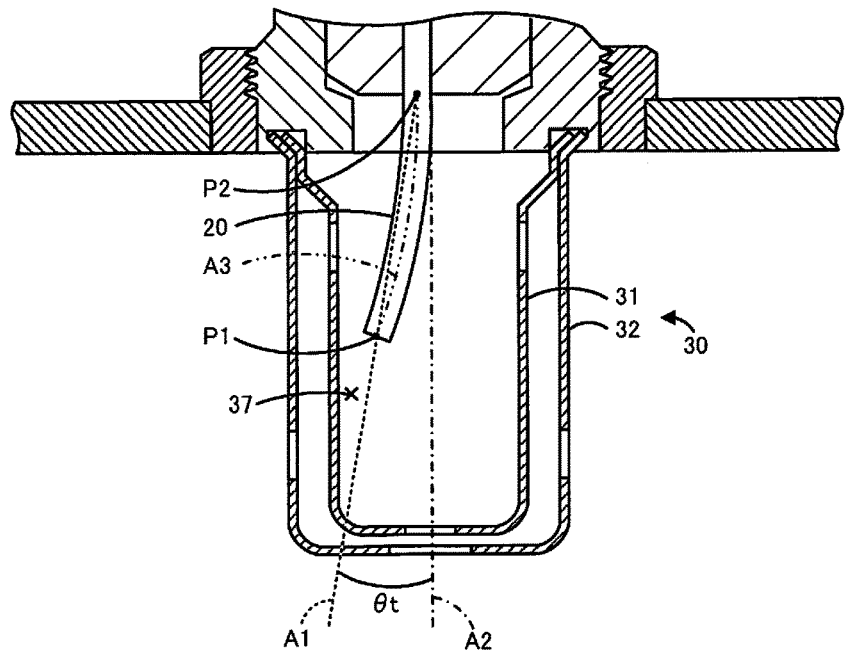
FIG. 4 is a diagram for explaining an axial direction of the sensor element 20 with warpage in the element chamber 37.

In the embodiments described above, the sensor element 20 has no warpage, and a portion of the sensor element 20 located inside the element chamber 37 and the other portion located outside the element chamber 37 have the same axial direction. However, the present invention is not limited to this. That is, the different portions of the sensor element 20 described above may have different axial directions, as long as the inclination angle θt, which is determined on the basis of the axial direction of the portion of the sensor element 20 located in the element chamber 37, is 1° or greater. If, for example, the sensor element 20 has warpage in the element chamber 37 and the axial line of the sensor element 20 is not straight at the portion in the element chamber 37, a direction parallel to a straight line connecting both ends of this axial line is defined as "the axial direction of the sensor element in the element chamber". FIG. 4 is a diagram for explaining the axial direction of the sensor element 20 with warpage in the element chamber 37. In FIG. 4, a straight line (broken line) connecting points P1 and P2 at both ends of an axial line A3 (two-dot chain line) of the portion of the sensor element 20 in the element chamber 37 is defined as the element axis A1, and a direction parallel to the element axis A1 is defined as the axial direction of the sensor element 20 in the element chamber 37. An angle formed by the direction parallel to the element axis A1 and a direction parallel to the cover axis A2 is defined as the inclination angle θt.

In the embodiments described above, the first insulator 45 and the seal material 49 each have an inclined through-hole, into which the sensor element 20 is inserted and secured in place at the inclination angle θt. However, the present invention is not limited to this. In the gas sensor 10, the sensor element 20 may be secured in any manner as long as the inclination angle θt is 1° or greater. For example, the sensor element 20 may be formed in a warped state, and the first insulator 45 and the seal material 49 may each have a through-hole shaped to accommodate this warpage. If the sensor element 20 has no warpage, the sensor element 20 may be pushed by the shape of the through-holes of the first insulator 45 and the seal material 49 so that the sensor element 20 is warped (or bent) to adjust the inclination angle θt to 1° or greater.

The shape of the protective cover 30 is not limited to the embodiments described above. For example, at least one of the inner protective cover 31 and the outer protective cover 32 may have a stepped portion formed by axially connecting a large-diameter portion on the proximal side to a small-diameter portion on the distal side. The arrangement and number of the element chamber inlets 33, the element chamber outlet 34, the outer inlets 35, and the outer outlet 36 are not limited to those described in the embodiments. Although the element chamber inlets 33, the element chamber outlet 34, the outer inlets 35, and the outer outlet 36 are circular holes in the embodiments described above, their shape is not limited to this. That is, they may be oval holes, polygonal (e.g., rectangular) holes, or slit-like openings, not holes. Although the protective cover 30 is of a so-called aspirator type (which may also be referred to as a differential-pressure aspiration type) in the embodiments described above, the type of the protective cover 30 is not particularly limited to this. That is, the measured gas may flow in and out of the protective cover 30 without using a differential pressure between the vicinity of the inner periphery of the pipe 90 and the vicinity of the central axis of the pipe 90. Although the protective cover 30 has a two-layer structure of the inner protective cover 31 and the outer protective cover 32 in the embodiments described above, the structure of the protective cover 30 is not limited to this. That is, the protective cover 30 may have a three or more layer structure, or may have a single-layer structure formed by one of the inner protective cover 31 and the outer protective cover 32. Although the protective cover 30 (i.e., the inner protective cover 31 and the outer protective cover 32) is a cylindrical member in the embodiments described above, the protective cover 30 may be of any shape as long as it is tubular.

In the embodiments described above, the protective layer 29 has a greater thickness at a portion covering the surface of the sensor element 20 on the inclination side in the element chamber 37 than at a portion covering the surface of the sensor element 20 opposite the inclination side in the element chamber 37. However, the present invention is not particularly limited to this. The protective layer 29 covering the different faces of the sensor element 20 in the element chamber 37 may have a uniform thickness. Although the protective layer 29 covers the distal face 20a and the first to fourth faces 21a to 21d in the embodiments described above, at least one of these five faces does not necessarily need to be covered. The gas sensor 10 does not necessarily need to include the protective layer 29. Note that "the protective layer 29 has a greater thickness at a portion covering the surface of the sensor element 20 on the inclination side in the element chamber 37 than at a portion covering the surface of the sensor element 20 opposite the inclination side in the element chamber 37" means that as long as the protective layer 29 covers the surface of the sensor element 20 on the inclination side, the protective layer 29 does not necessarily need to cover the surface of the sensor element 20 opposite the inclination side.

Although the measured gas introduction port 22a is provided in the distal face 20a of the sensor element 20 in the embodiments described above, the measured gas introduction port 22a may be provided in another face of the sensor element 20 as long as it is located in the element chamber 37. For example, the measured gas introduction port 22a may be provided in the first face 21a. This also has the effect of improving the responsiveness of the gas sensor 10 as long as the inclination angle θt is 1° or greater. If the measured gas introduction port 22a is provided in the first face 21a, the element chamber inlets 33 in the inner protective cover 31 may be located above the measured gas introduction port 22a (i.e., located closer to the proximal face 20b of the sensor element 20 than the measured gas introduction port 22a is).

The configuration of the detecting portion 23 is not limited to that in the embodiments described above. The number and arrangement of electrodes included in the detecting portion 23 may differ from those in the embodiments described above. For example, the detecting portion 23 does not necessarily need to include the inner auxiliary pump electrodes 26. Although a part of the detecting portion 23 (i.e., the inner main pump electrodes 25, the inner auxiliary pump electrodes 26, and the measurement electrode 27) is disposed in the interior of the sensor element 20 extending from the measured gas introduction port 22a in the embodiments described above, the present invention is not limited to this. For example, the sensor element 20 does not necessarily need to have the measured gas introduction port 22a. In this case, for example, the detecting portion 23 may include at least the measurement electrode 27 and the reference electrode 28, and the measurement electrode 27 may be disposed on a surface (e.g., first face 21a) of the sensor element 20.

Although the sensor element 20 has a long plate-like shape in the embodiments described above, the sensor element 20 may be of any shape as long as it is a long element. For example, the sensor element 20 may have a columnar shape.

EXAMPLES

Gas sensors that were specifically made will now be described as examples. Experimental examples 2 to 10 correspond to examples of the present invention, and Experimental example 1 corresponds to a comparative example. The present invention is not limited to the examples described below.

Experimental Examples 1 to 10

The gas sensors (Experimental examples 1 to 10) having the same configuration as the gas sensor 10 in FIGS. 2 and 3, except for their inclination angles θt (see Table 1) and having no protective layer 29, were made. The inside diameter of the inner protective cover 31 was 8 mm. The element chamber inlets 33 were circular in shape with a diameter of 2 mm, and six element chamber inlets 33 were formed in the outer periphery of the inner protective cover 31 at regular intervals. The element chamber outlet 34 was circular in shape with a diameter of 2 mm. The inside diameter of the outer protective cover 32 was 12 mm. The outer inlets 35 were circular in shape with a diameter of 3 mm, and six outer inlets 35 were formed in the outer periphery of the outer protective cover 32 at regular intervals. The outer outlet 36 was circular in shape with a diameter of 3 mm. As in FIG. 2, each of the sensor elements 20 in Experimental examples 2 to 10 was inclined in the direction in which the distal portion of the sensor element 20 was moved from the position of the second face 21*b* toward the first face 21*a*.

(Responsiveness Test)

For the gas sensors of Experimental examples 1 to 10, the responsiveness of each sensor element 20 in detecting a specified gas concentration was evaluated. Specifically, the evaluation was made in the following manner. First, the gas sensor of Experimental example 1 was attached to a pipe as in FIG. 1. The pipe was 50 mm in diameter. The length of a portion of the protective cover 30 protruding into the pipe (i.e., length in the vertical direction in FIG. 2) was 28 mm. Air was allowed to flow into the pipe at a flow velocity of 5 m/sec and stand for sufficient time. The gas flowing in the pipe was then switched from air to the measured gas. The measured gas, which was nitrogen containing 500 ppm of NO, was allowed to flow at a flow velocity of 5 m/sec. The direction of flow of the air and measured gas in Experimental example 1 was from left to right in FIG. 2. The change in the output of the sensor element 20 (i.e., an electric signal generated by the detecting portion 23) with respect to time in this case was examined. With the output of the sensor element 20 during flow of air in the pipe being taken as 0% and the maximum output of the sensor element 20 during flow of measured gas in the pipe being taken as 100%, the time elapsed from when the output exceeded 10% to when it exceeded 90% was measured and defined as a response time (msec) in detecting a specified gas concentration. A shorter response time means higher responsiveness of the gas sensor in detecting a specified gas concentration. For Experimental examples 2 to 10, the response time was measured in the same manner as above. The inclination angle θt and the response time measured in the test for each of Experimental examples 1 to 10 are shown in Table 1.

TABLE 1

|  | Inclination angle θt[°] | Response time [msec] |
| --- | --- | --- |
| Experimental example 1 | 0 | 400 |
| Experimental example 2 | 1 | 350 |
| Experimental example 3 | 3 | 320 |
| Experimental example 4 | 5 | 300 |
| Experimental example 5 | 7 | 250 |
| Experimental example 6 | 9 | 200 |
| Experimental example 7 | 11 | 200 |
| Experimental example 8 | 13 | 250 |
| Experimental example 9 | 15 | 300 |
| Experimental example 10 | 17 | 350 |

As in Table 1, the response time in Experimental example 0.2 where the inclination angle θt was 1° was shorter than that in Experimental example 1 where the inclination angle θt was 0°. The response time had a tendency to decrease as the inclination angle θt increased from 1°. Thus, the result indicates that the inclination angle θt is preferably 3° or greater, more preferably 5° or greater, and still more preferably 9° or greater. Table 1 also shows that the response time had a tendency to increase when the inclination angle θt was too large. This indicates that to reduce an increase in response time, the inclination angle θt is preferably 15° or less, more preferably 13° or less, and still more preferably 11° or less. The response time was shortest when the inclination angle θt was greater than 7° and less than 13°.

The present application claims priority of Japanese Patent Application No. 2015-191249 filed on Sep. 29, 2015, the entire contents of which are incorporated herein by reference.

What is claimed is:

1. A gas sensor comprising:
   a tubular protective cover having an element chamber therein and configured to allow a measured gas to flow from the outside into the element chamber; and
   a long sensor element including a detecting portion located in the element chamber and configured to detect a specified gas concentration in the measured gas,
   wherein an inclination angle θt of an axial direction of the sensor element in the element chamber with respect to an axial direction of the protective cover is greater than or equal to 5° and less than or equal to 20°.

2. The gas sensor according to claim 1, wherein the inclination angle θt of the sensor element is 15° or less.

3. The gas sensor according to claim 1, further comprising a protective layer having a greater thickness at a portion covering a surface of the sensor element on an inclination side in the element chamber than at a portion covering a surface of the sensor element opposite the inclination side in the element chamber.

4. The gas sensor according to claim 1, wherein the protective cover has an element chamber inlet open to the element chamber and serving as a passage of the measured gas; and an element chamber outlet open to the element chamber, serving as a passage of the measured gas, and located closer to a distal end of the protective cover than the element chamber inlet is.

5. The gas sensor according to claim 1, wherein the sensor element has a plate-like shape and a portion of the sensor element, the portion being located in the element chamber, is inclined in a thickness direction of the sensor element with respect to the axial direction of the protective cover.

* * * * *